United States Patent [19]
Garleb et al.

[11] Patent Number: 5,688,777
[45] Date of Patent: Nov. 18, 1997

[54] INHIBITION OF C. DIFFICILE INFECTIONS BY INDIGESTIBLE OLIGOSACCHARIDES

[75] Inventors: Keith Allen Garleb, Powell; Bryan Warren Wolf, Newark, both of Ohio; Jonathan Allan Meulbroek, Grayslake, Ill.; Keith Brian Wheeler, Dublin, Ohio

[73] Assignee: Abbott Laboratories, Abbott Park, Ill.

[21] Appl. No.: 417,413

[22] Filed: Apr. 5, 1995

[51] Int. Cl.$^6$ ............................................. A01N 43/04
[52] U.S. Cl. ........................ 514/54; 514/183; 514/449; 514/451; 514/453; 514/455; 514/456; 514/461
[58] Field of Search ........................... 514/54, 183, 449, 514/451, 453, 455, 456, 461

[56] References Cited

U.S. PATENT DOCUMENTS

| | | | |
|---|---|---|---|
| 4,681,771 | 7/1987 | Adachi et al. | 426/658 |
| 5,219,842 | 6/1993 | Okada et al. | 514/54 |
| 5,444,054 | 8/1995 | Garleb et al. | 514/54 |

OTHER PUBLICATIONS

Bryant et al., Journal of Dairy Science, 36:205–217 (1953).
Gill et al., Journal of Animal Sciences, 33:331–336 (1971).
Lusk et al., The Journal of Infectious Diseases, 137(4):464–475 (1978).
George et al., Journal of Clinical Microbiology, 9:214–219 (1979).
Price et al., Gut, 20:467–475 (1979).
Mulligan et al., Current Microbiology, 3:173–175 (1979).
Bartlett et al, Gastroenterology, 78:431–434 (1980).
Banno et al., Biochemistry International, 2(6):625–635 (1981).
Wilson et al., Infection and Immunity, 34(2):626–628 (1981).
Taylor et al., Infection and Immunity, 34:1036–1043 (1981).
Sullivan et al., Infection and Immunity, 35(3):1032–1040 (1982).
Walters et al., Gut, 24:206–212 (1983).
Pocock, Clinical Trials: A Practical Approach, John Wiley & Sons Ltd., NY, NY. (1983) pp. 13 and 222–225.
Wilson et al., The Journal of Infectious Diseases, 151(2):355–361 (1985).
Rosner, Fundamentals of Biostatistics, PWS Publishers, Boston, MA, (1986), pp. 286–292.
Bender et al., The Lancet, 2:11–13 (1986).
Wilson et al., The Journal of Infectious Diseases, 153(3):547–551 (1986).
Meyer et al., Applied and Environmental Microbiology, 51(3):622–629 (1986).
Triadafilopoulos et al., Gastroenterology, 93:273–279 (1987).
Mackie et al., Applied and Environmental Microbiology, 54(9):2155–2160 (1988).
McFarland et al., The New England Journal of Medicine, 320(4):204–210 (1989).
Fekety et al., The American Journal of Medicine, 86:15–19 (1989).
Bennett et al., Geriatrics, 45(9):77–87 (1990).
Thomas et al., Journal of the American Geriatrics Society, 38:415–420 (1990).
Brown et al., Infection Control Hospital Epidemiology, 11(6):283–290 (1990).
McFarland et al., The Journal of Infectious Diseases, 162:678–684 (1990).
Kimmey et al., Digestive Diseases and Sciences, 35(7):897–901 (1990).
Johnson et al., Annals of Internal Medicine, 117(4):297–302 (1990).
Okazaki et al., Bifidobacteria Microflora, 9(2):77–86 (1990).
Imaizumi et al., Agricultural and Biological Chemistry, 55(1):199–205 (1991).
Kofsky et al., Diseases of the Colon and Rectum, 34:244–248 (1991).
Fekety, Diarrheal Diseases, ed. Field, (1991) pp. 293–317.
Hidaka et al., Journal of Carbohydrate Chemistry, 10(4):509–522 (1991).
Fekety et al., Journal of the American Medical Association, 269(1):71–75 (1993).
Kelly et al., The New England Journal of Medicine, 330(4):257–262 Jan. 1994.
McFarland et al., Journal of the American Medical Association, 271(24):1913–1918 Jun. 1994.

*Primary Examiner*—James J. Seidleck
*Assistant Examiner*—John M. Cooney, Jr.
*Attorney, Agent, or Firm*—L. R. Drayer; D. O. Nickey

[57] ABSTRACT

The primary etiology of antibiotic-associated diarrhea (which may lead to pseudomembranous colitis) has been recognized as *Clostridium difficile*. It is believed that the indigenous microflora of a healthy individual suppresses the normally present *C. difficile*. However, when the indigenous microflora are disrupted (e.g., during antibiotic treatment) overgrowth of *C. difficile* may occur causing diarrhea and colitis. Treatment of *C. difficile* with antibiotics has proven effective, but many times relapse occurs. The present invention involves a non-antibiotic approach to the treatment and/or prevention of *C. difficile*—associated diseases. A therapeutically effective amount of an indigestible oligosaccharide inhibits the infection of mammals by *C. difficile* when administered enterally.

5 Claims, 8 Drawing Sheets

$1^F$-β-FRUCTOFURANOSYL NYSTOSE

NYSTOSE

1-KETOSE

INHIBITION OF *C. DIFFICILE* INFECTIONS BY INDIGESTIBLE OLIGOSACCHARIDES

FIELD OF THE INVENTION

This invention relates to the use of indigestible oligosaccharides in the inhibition of disease states by *Clostridium difficile*.

BACKGROUND OF INVENTION

*Clostridium difficile* (*C. difficile*) is the leading known cause of nosocomial infections. Greenough et al., "Diarrhea in the elderly", *PRINCIPLES OF GERIATRIC MEDICINE AND GERONTOLOGY*, Hazzard, et al., (ed) New York, McGraw-Hill, pp. 1168–1176 (1990); MeFarland et al., "A Randomized Placebo-Controlled Trial of *Saccharomyces boulardii* in Combination with Standard Antibiotics for *Clostridium difficile* Disease", *JOURNAL OF THE AMERICAN MEDICAL ASSOCIATION*, 271(24):1913–1918 (1994). The greatest risk of obtaining *C. difficile* infection usually involves a surgical procedure (normally gastrointestinal in nature) combined with antibiotic therapy. Often, diets consumed by such patients are not conducive to either establishment or maintenance of the normal intestinal bacteria. In addition, *C. difficile* may be endemic in long-term care facilities for the elderly where outbreaks of diarrhea are common. Bender et al., "Is *Clostridium difficile* endemic in chronic-care facilities?", *THE LANCET*, 2:11–13 (1986).

There are also economic consequences to infection by this pathogen since patients who acquire diseases caused by *C. difficile* require longer hospital stays resulting in additional health care costs. Kofsky et al., "*Clostridium difficile*—a common and costly colitis", *DISEASES OF THE COLON AND RECTUM*, 34:244–248 (1991) noted that *C. difficile* infections result in an additional $2,000 to $5,000 per episode to the cost of health care. Furthermore, patients who are infected during a hospital stay have been shown to spread infection to extended care facilities and to their environment. Bender et al., "Is *Clostridium difficile* endemic in chronic-care facilities?", *THE LANCET*, 2:11–13 (1986); Bennet I et al., "*C. difficile* diarrhea: A common-and overlooked-nursing home infection", *GERIATRICS*, 45(9):77–87 (1990); Kofsky et al., "*Clostridium difficile*—a common and costly colitis", *DISEASES OF THE COLON AND RECTUM*, 34:244–248 (1991); Mulligan et al., "Contamination of a Hospital Environment by *Clostridium difficile*", *CURRENT MICROBIOLOGY*, 3:173–175 (1979). Thomas et al., "Postantibiotic colonization with *Clostridium difficile* in nursing home patients", *JOURNAL OF THE AMERICAN GERIATRICS SOCIETY*, 38:415–420 (1990) noted that ". . . postantibiotic *C. difficile* infection serves as a marker of death in nursing-home patients, one that can be differentiated from the risk of antibiotic treatment alone."

*C. difficile* is a spore-forming, obligate anaerobic bacillus. It is a component of the normal intestinal flora of about 3% to 5% of healthy adults, but can be found in the stools of up to 15% to 20% of adults who are patients in hospitals and as many as 50% of asymptomatic infants. Fekety, "Antibiotic-Associated Diarrhea", *DIARRHEAL DISEASES*, ed. Field, pp. 293–317 (1991).

When established in the colon, pathogenic strains of *C. difficile* produce toxins that are the cause of diarrhea and colitis. Banno et al., "Two toxins (D-1 and D-2) of *Clostridium difficle* causing antibiotic-associated colitis: Purification and some characterization", *BIOCHEMISTRY INTERNATIONAL.*, 2(6):625–635 (1981); Taylor et al., "Comparison of two toxins produced by *Clostridium difficle*", *INFECTION AND IMMUNITY*, 34:1036–1043 (1981). *C. difficile* produces two large protein exotoxins known as toxin A and toxin B. Toxin A causes fluid secretion, mucosal damage, and intestinal intimation when injected into rodent intestine. Triadafilopoulos et al., "Differential effects of *Clostridium difficle* toxins A and B on rabbit ileum", *GASTROENTEROLOGY*, 93:273–279 (1987). Toxin B is more potent than toxin A as a cytotoxin in tissue culture, but is not enterotoxic in animals. Kelly et al., "*Clostridium difficle* Colitis", *THE NEW ENGLAND JOURNAL OF MEDICINE*, 330(4):257–262 (1994).

Toxin A (known as Toxin D-2 in the Japanese literature) is an enterotoxin and is considered the primary mediator of *C. difficile*-associated disease. It has a molecular weight (MW) of approximately 308,000. Toxin B (known as Toxin D-1 in the Japanese literature) is a cytotoxin and has a molecular weight of approximately 270,000. It is believed that Toxin A causes tissue damage within the gastrointestinal tract and this damage is exacerbated by Toxin B resulting in diarrhea and colitis.

Infection with *C. difficile* manifests itself clinically as uncomplicated diarrhea, nonspecific colitis, or most seriously as pseudomembranous colitis (PMC). Dehydration as a result of diarrhea often follows *C. difficile* infection. Death may occur from complications such as toxic megacolon or intestinal perforation. McFarland et al., "Nosocomial Acquisition of *Clostridium difficile* Infection", *THE NEW ENGLAND JOURNAL OF MEDICINE*, 320(4):204–210 (1989); Brown et al., "Risk Factors for *Clostridium difficile* Toxin-Associated Diarrhea", *INFECTION CONTROL HOSPITAL EPIDEMIOLOGY*, 11(6):283–290 (1990). *C. difficile* colitis occurs at all ages, but is most frequent in elderly and debilitated patients. It is relatively rare in infants even though the organism is commonly found in their stools and usually only follows antibiotic use. Fekety, "Antibiotic-Associated Diarrhea", *DIARRHEAL DISEASES*, Field (ed.), published by Elsevier, pp.293–317 (1991). Infection by *C. difficile* is responsible for all cases of pseudomembranous colitis and for up to 20% of cases of antibiotic-associated diarrhea without colitis. Kelly et al., "*Clostridium difficile* Colitis", *THE NEW ENGLAND JOURNAL OF MEDICINE*, 330(4):257–262 (1994); McFarland et al., "Risk factors for *Clostridium difficile* carriage and *C. difficile*-associated diarrhea in a cohort of hospital patients", *THE JOURNAL OF INFECTIOUS DISEASES* 162:678–684 (1990).

The persistence of *C. difficile* as a nosocomial pathogen is facilitated by the ease with which it is transmitted within the hospital environment and by the widespread use of antibiotics. Antibiotics given for the treatment of even minor infections and administered by any route may precipitate PMC. Practically every antimicrobial used in the treatment of human infections, including those most commonly used in the treatment of the disease, is known to incite PMC. Fekety, "Antibiotic-Associated Diarrhea", *DIARRHEAL DISEASES*, Field (ed.), published by Elsevier, pp. 293–317 (1991). PMC may occur during the period immediately (almost always within 6 weeks) after the use of antibiotics have been discontinued, during this period, the normal intestinal flora has not yet reached normal levels, this absence of normal flora permits *C. difficile* to grow to unhealthy population levels. Fekety, "Antibiotic-Associated Diarrhea", *DIARRHEAL DISEASES*, Field (ed.), published by Elsevier, pp. 293–317 (1991). The standard treatment for *C. difficile*-associated disease is administration of the antibiotics vancomycin or metronidazole. No new antibiotic treatments have proven to be effective in clinical trials. Fekety et al., "Diagnosis and Treatment of *Clostidium difficile* colitis", *JOURNAL OF THE AMERICAN MEDICAL ASSOCIATION*, 269(1):71–75 (1993); Kelly et al., "*Clostridium difficle* Colitis", *THE NEW ENGLAND JOURNAL OF MEDICINE*, 330(4):257–262 (1994). Standard antibiotic therapy is effective in 80% of patients with *C. difficile*-associated disease (CDD), but the remaining 20% experience further episodes of diarrhea or colitis during the permissive period after the antibiotic has been discontinued. Fekety et al., "Treatment of Antibiotic-Associated *Clostridium difficile* Colitis with Oral Vancomycin: Comparison of Two Dosage Regimens", *THE AMERICAN JOURNAL OF MEDICINE*, 86:15–19 (1989); Walters et al., "Relapse of antibiotic associated colitis: endogenous persistence of *Clostridium difficile* during vancomycin therapy", *GUT* 24:206–212 (1983); Bartlett et al., "Symptomatic Relapse After Oral Vancomycin Therapy of Antibiotic-Associated Pseudomembranous Colitis", *GASTROENTEROLOGY*, 78:431–434 (1980). Once patients have had one recurrence, they may experience repeated episodes of disease over several years. Fekety et al., "Diagnosis and Treatment of *Clostridium difficile* colitis", *JOURNAL OF THE AMERICAN MEDICAL ASSOCIATION*, 269 (1):71–75 (1993); Kimmey et al., "Prevention of Further Recurrences of *Clostridium difficile* Colitis with *Saccharomyces boulardii*", *DIGESTIVE DISEASES AND SCIENCES*, 35(7):897–901 (1990). In a randomized, placebo-controlled trial, Johnson et al., "Treatment of asymptomatic *Clostridium difficle* carriers (fecal excretors) with vancomycin or metronidazole", *ANNALS OF INTERNAL MEDICINE*, 117(4):297–302(1990), compared the efficacy of vancomycin and metronidazole for eradicating asymptomatic *C. difficile* fetal excretors as a means of controlling nosocornial outbreaks of *C. difficile* diarrhea. They found that metronidazole was not effective, and even though vancomycin was temporarily effective, it was associated with a significantly higher rate of *C. difficile* carriage 2 months after treatment. In their conclusions, they did not recommend antibiotic treatment of asymptomatic patients excreting *C. difficile*.

Given the causative role played by antibiotics in CDD, however, investigating alternatives to antibiotics might be a more effective strategy for developing new treatments for these debilitating conditions. The significant clinical burden of CDD and the role of antibiotics in causing these diseases underscores the importance of developing alternative methods of prevention and treatment.

There is provided in accordance with one aspect of the present invention a method of inhibiting the infection of a mammal by *Clostridium difficile* by enterally administering a therapeutically effective amount of an indigestible oligosaccharide.

There is provided in accordance with another aspect of the invention a method of inhibiting the level of toxin A from *Clostridium difficile* in a mammal by enterally administering a therapeutically effective amount of an indigestible oligosaccharide.

DETAILED DESCRIPTION OF THE INVENTION

As used herein and in the claims "indigestible oligosaccharide" refers to a small carbohydrate moiety (Degree of polymerization less than 20 and/or a molecular weight less than 3,600) that is resistant to endogenous digestion in the human upper digestive tract. Indigestible oligosaccharides that may be employed in preferred embodiments of the invention are fructooligosaccharides and xylooligosaccharides. Indigestible oligosaccharides that may be employed in most preferred embodiments of the invention are fructooligosaccharides selected from the group consisting of 1-ketose, nystose and $1^F$-β-fructofuranosyl nystose fructooligosaccharides, and xylooligosaccharides selected from the group consisting of xylobiose, xylotriose and xylotetrose xylooligosaccharides.

Fructooligosaccharides (FOS) are carbohydrate polymers consisting of a chain of fructose residues linked by $(2 \rightarrow 1)$ -β-glucosidic bonds and usually carry a single D-glucosyl residue at the non-reducing end of the chain linked $(1 \rightarrow 2)$ -α- as in sucrose.

Figure 1C:
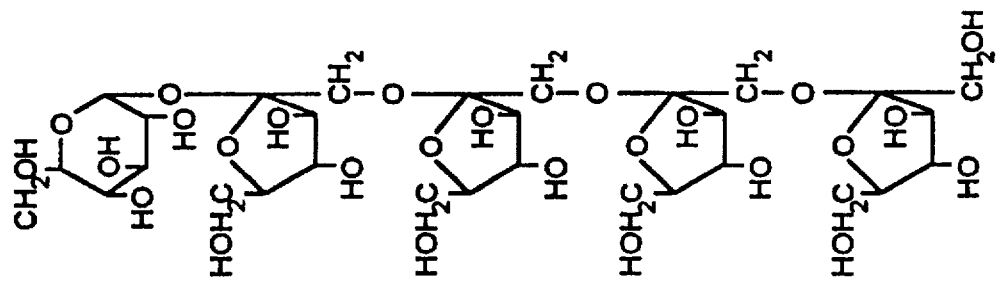
FIGS. 1A, 1B and 1C are representations of the chemical structures of fructoologosaccharides having utility in the practice of the present invention.
Figure 1B:
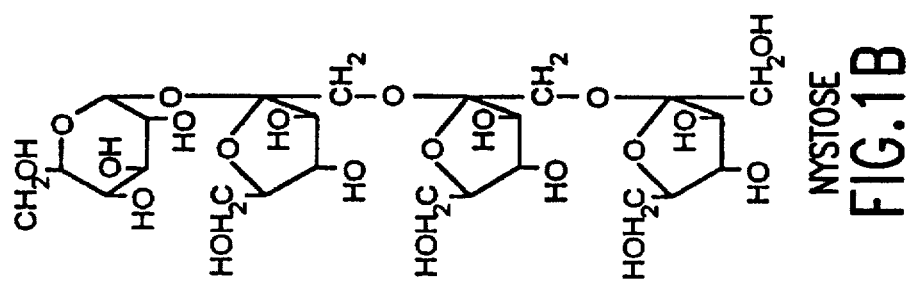
Figure 1A:
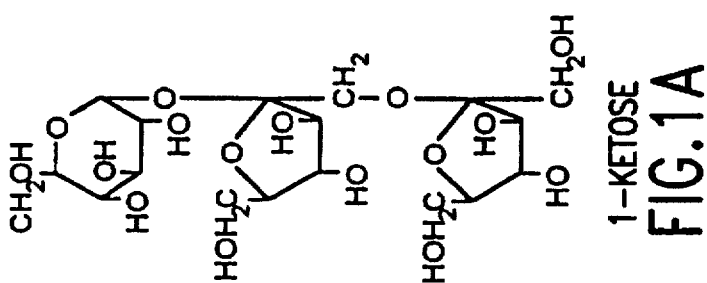

FOS occur in nature in many kinds of plants including bananas, tomatoes, onions, wheat, barley, honey, asparagus and artichokes. They can also be synthesized from sucrose through the use of transfructosylating enzymes, such as the enzyme obtained from the fungus *Aspergillus niger*. Hidaka et al., "Fructooligosaccharides: Enzymatic Preparation and Biofunctions", *JOURNAL OF CARBOHYDRATE CHEMISTRY*, 10(4):509–522 (1991). Treatment of sucrose with this enzyme results in a mixture of fructooligosaccharides containing 2, 3, or 4 fructose residues. The resulting fructooligosaccharides are designated respectively 1-ketose ($GF_2$), nystose ($GF_3$), and $1^F$-β-fructofuranosyl nystose ($GF_4$), the chemical structures of which are depicted in FIG. 1. A method of producing FOS industrially is disclosed in U.S. Pat. No. 4,681,771 to Adachi et al.

FOS are not hydrolyzed in the small intestine by rat or human digestive enzymes and thus reach the large intestine intact. There, many intestinal microorganisms utilize them. FOS can be utilized most significantly by bifidobacteria, which are believed to be highly beneficial organisms (Hidaka et al.). They cannot be utilized in vitro by certain undesirable, putrefactive bacteria such as *C. perfringens, C. difficile*, or *E. coli*.

Carbohydrates which are not digested in the small intestine can be fermented to short chain fatty acids by the microorganisms found in the large intestine. The short chain fatty acids are used as an energy source for colonocytes and other organs such as the liver. FOS have also been shown to reduce total serum cholesterol, probably by reducing the level of LDL-cholesterol, and to alleviate constipation by accelerating peristaltic movement (Hidaka et al.).

Figure 2A:
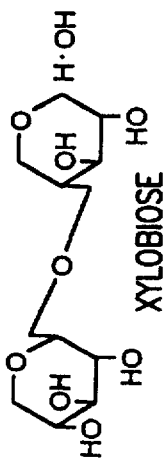
FIGS. 2A, 2B and 2C are representations of the chemical structures of xylooligosaccharides having utility in the practice of the present invention.
Figure 2B:
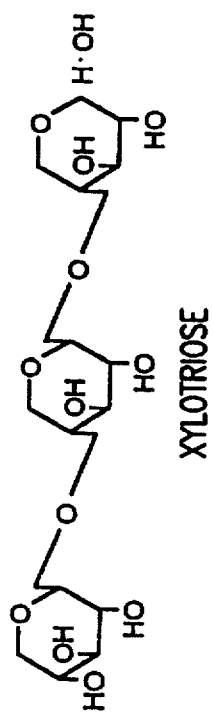
Figure 2C:
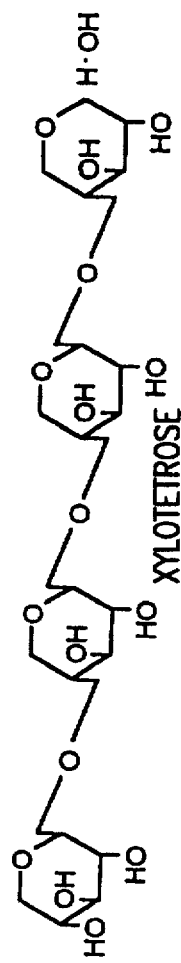

Xylooligosaccharides (XOS) are prepared by the enzymatic hydrolysis of the xylan from corn, sugar cane, and cottonseed. Xylans are hydrolyzed by a Trichoderma-derived enzyme xylanase to make XOS. Xylooligosaccharides are mainly composed of two, three and four xylose units with a β-1-4 linkage, xylobiose, xylotriose and xylotetrose, respectively the chemical structures of which are depicted in FIG. 2. Xylobiose, the main component of XOS, is relatively abundant in bamboo shoots. Imaizumi et al., "Effects of xylooligosaccharides on blood glucose, serum and liver lipids and cecum short-chain fatty acids in diabetic rats", *AGRICULTURAL AND BIOLOGICAL CHEMISTRY*, 5(1): 199–205,(1991 ).

XOS, like FOS, have been shown to be selectively utilized by Bifidobacteria in vitro Okazaki et al., "Effect of xylooligosaeeharide on the growth of bifidobacteria", *BIFIDOBACTERIA MICROFLORA*, 9(2):77–86 (1990). In addition, clinical studies have shown that XOS, when supplemented to human diets, increase the level of bifidobacteria recovered in the feces (Okazaki et al). Furthermore, in vitro studies demonstrate that potential pathogens like Staphylococcus, *E. coli, C. perfringens,* and *C. difficile* are not able to utilize XOS as an energy source (Okazaki et al).

The non-digestibility of indigestible oligosaccharides, like XOS and FOS, and their selective utilization by beneficial intestinal bacteria leads to an increase in the presence of bifidobacteria and results in the production of short chain fatty acids, which may lower pH in the large intestine, and suppress undesirable microorganisms and the substances (e.g., toxins) they produce. These activities would be beneficial to both human and animal health.

Two experiments were conducted to determine the effect of fructooligosaccharides (FOS) as a dietary supplement on mortality in a Syrian hamster model of *C. difficile*-colitis.

ANIMAL MODEL FOR EXPERIMENTS 1 AND 2

The use of the Syrian hamster as a model for *C. difficile*-colitis is widely recognized. Lusk et al., "Clindamycin-Induced Enterocolitis in Hamsters", THE JOURNAL OF INFECTIOUS DISEASES, 173(4):464–475-(1978), proposed that the enterocolitis induced in the hamster by antibiotics is a good model for investigation of the syndrome in humans. Price et al "Morphology of experimental antibiotic-associated enterocolitis in the hamster: a model for human pseudomembranous colitis and antibiotic-associated diarrhoea", GUT, 20:467–475 (1979) set out to study the morphology of experimental antibiotic-associated pseudomembranous colitis (PMC). They noted that the hamster model has some morphological differences; however, the bacteriology and toxicology are identical to the human. They concluded that the hamster is a good model for investigating the pathogenesis of PMC and antibiotic-associated enteropathy in general. In fact, Wilson et al., "Suppression of *Clostridium difficile* by Normal Hamster Cecal Flora and Prevention of Antibiotic-Associated Cecitis", INFECTION AND IMMUNITY, 34(2):626–628 (1981), noted that studies with the hamster model of antibiotic-associated colitis led to the discovery of *C. difficile* toxin as a major etiology of antibiotic-associated colitis in humans and to effective treatment with oral vancomycin. Wilson et al., "Population Dynamics of Ingested *Clostridium difficile* in the Gastrointestinal Tract of the Syrian Hamster", THE JOURNAL OF INFECTIOUS DISEASES, 151(2):355–361 (1985) noted that the best studied animal model of antibiotic-associated colitis was that of the Syrian hamster.

MATERIALS AND METHODS FOR EXPERIMENTS 1 AND 2

Animals

Female golden Syrian hamsters (6–8 weeks old, 80–120 g) were purchased from Harlan Sprague Dawley, Inc., Indianapolis, Ind. Animals were randomly allotted to treatment groups and housed at 22°±2° C. in group housing. They were obtained pathogen free and housed in accordance with the Institutional Animal Care Use Committee (IACUC) and the American Association for the Accrediation of Laboratory Animal Care (AAALAC) standards. Animals were fed a standard lab chow diet (PROLAB®, Agway Country Foods, Inc., Syracuse, N.Y.).

Antibiotic

Hamsters were medicated by daily gavage with ciprofloxacin (Miles, Inc., West Haven, Conn.; 250 mg/kg of body weight/day) on day 0 through day 6. This medication results in an "antibiotic sterilization" of the gastrointestinal tract which allows natural infection (overgrowth) of *C. difficile*. This "natural" infection can be unreliable under a laboratory setting, thus for a consistent degree of infection between animals additional treatments were added to our experiments to include inoculation (challenge) of hamsters with *C. difficile* on day 3 and day 7.

Inoculum

A human isolate of *C. difficile* (strain VPI 10463) which has been shown to produce high amounts of toxin A and B was used in our studies. Wilson et al., "Gnotobiotic models for study of microbial ecology of *Clostridium difficle* and *Escherichia coli*", THE JOURNAL OF INFECTIOUS DISEASES, 153(3):547–551 (1986); Sullivan et al., "Purification and characterization of toxins A and B of *Clostridium difficile*", INFECTION AND IMMUNITY, 35(3) :1032–1040 (1982). *C. difficile* VPI 10463 was grown in BHI (brain heart infusion, Difco Laboratories, Detroit, Mich.) broth on a rotating platform under anaerobic conditions. An overnight culture (ONC) has a concentration of about $10^9$ CFU/mL. Hamsters were inoculated with their respective volume of ONC via gayage on day 3 and day 7.

EXPERIMENTAL DESIGNS

EXPERIMENT 1

In the first experiment, 41 female golden Syrian hamsters were randomly allotted among 1 of 6 treatment groups. Treatments were arranged in a 2×3 factorial, with 2 levels of FOS (0 or 30 g/L in drinking water) and 3 levels of *C. difficile* (approximately $10^9$ CFU/mL) inoculation (0, 0.5, or 2.0 mL). Hamsters were orally treated with ciprofloxacin (250 mg/kg of body weight/day) from day 0 through day 6 and inoculated with their appropriate volume of an overnight culture of *C. difficile* on day 3 and day 7.

EXPERIMENT 2

In the second experiment, 63 hamsters were randomly allotted among 1 of 8 treatment groups. Treatments were arranged in a 2×2×2 factorial with 2 levels of FOS (0 or 30 g/L in drinking water), 2 levels of *C. difficile* inoculum (0 or 2.0 mL), and 2 levels of vancomycin (Eli Lilly, Indianapolis, Ind.) medication (0 or 50 mg/kg of body weight/day). FOS level, ciprofloxacin dose and inoculation protocol were similar to experiment 1. Hamsters on the vancomycin treatment were given 50 mg/kg of body weight/day on days 7 through 13.

DATA COLLECTION AND STATISTICS

EXPERIMENTS 1 AND 2

Upon death, survival time (in days) was recorded (measured from the first day of ciprofloxaein medication). Animals were followed through day 24 upon which day the experiment was terminated. Survival times were summarized as Kaplan-Meier curves (Pocock, CLINICAL TRIALS: A PRACTICAL APPROACH, John Wiley & Sons Ltd., New York, N.Y., USA (1983), pp. 13 and 222–225 Animals not expiring by the study's end had their survival times censored on day 24. FOS minus control group differences were tested by the log rank statistic, and supplemented with the generalized Wilcoxon test. In addition to the global analysis comparing FOS fed animals versus control (animals which were not fed FOS), marginal tests of treatment effect were performed for several subgroups; e.g., by level of *C. difficile* challenge. Test results are reported as two-sided, with statistical significance judged at the P less than 0.05 level. In general the results of the two statistical tests were similar. The Wilcoxon test (Rosner, FUNDAMENTALS OF BIOSTATISTICS, PWS Publishers, Boston, Mass., U.S.A. (1986), pp. 286–292 is designed to test the difference between treatments at earlier time points, while the log rank test (Neter and Wasserman, APPLIED LINEAR STATISTICAL MODELS, 1974, Richard D. Irwin, Inc., Homewood, Ill., USA (1974) is designed to test the difference between treatments at later time points.

RESULTS AND DISCUSSION

EXPERIMENT 1

Figure 3:
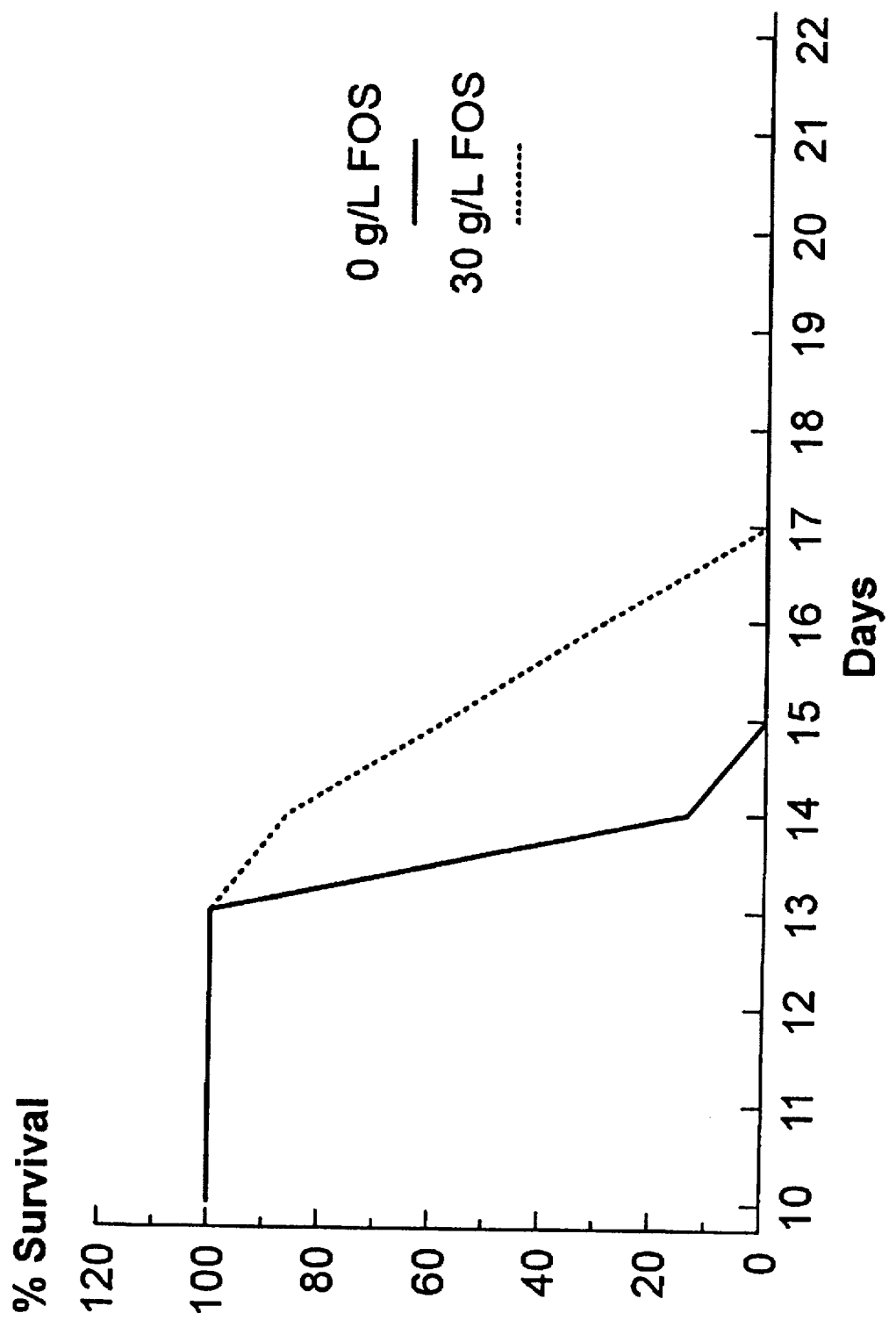
FIGS. 3 and 4 are graphic representations of the results of Experiment 1.
Figure 4:
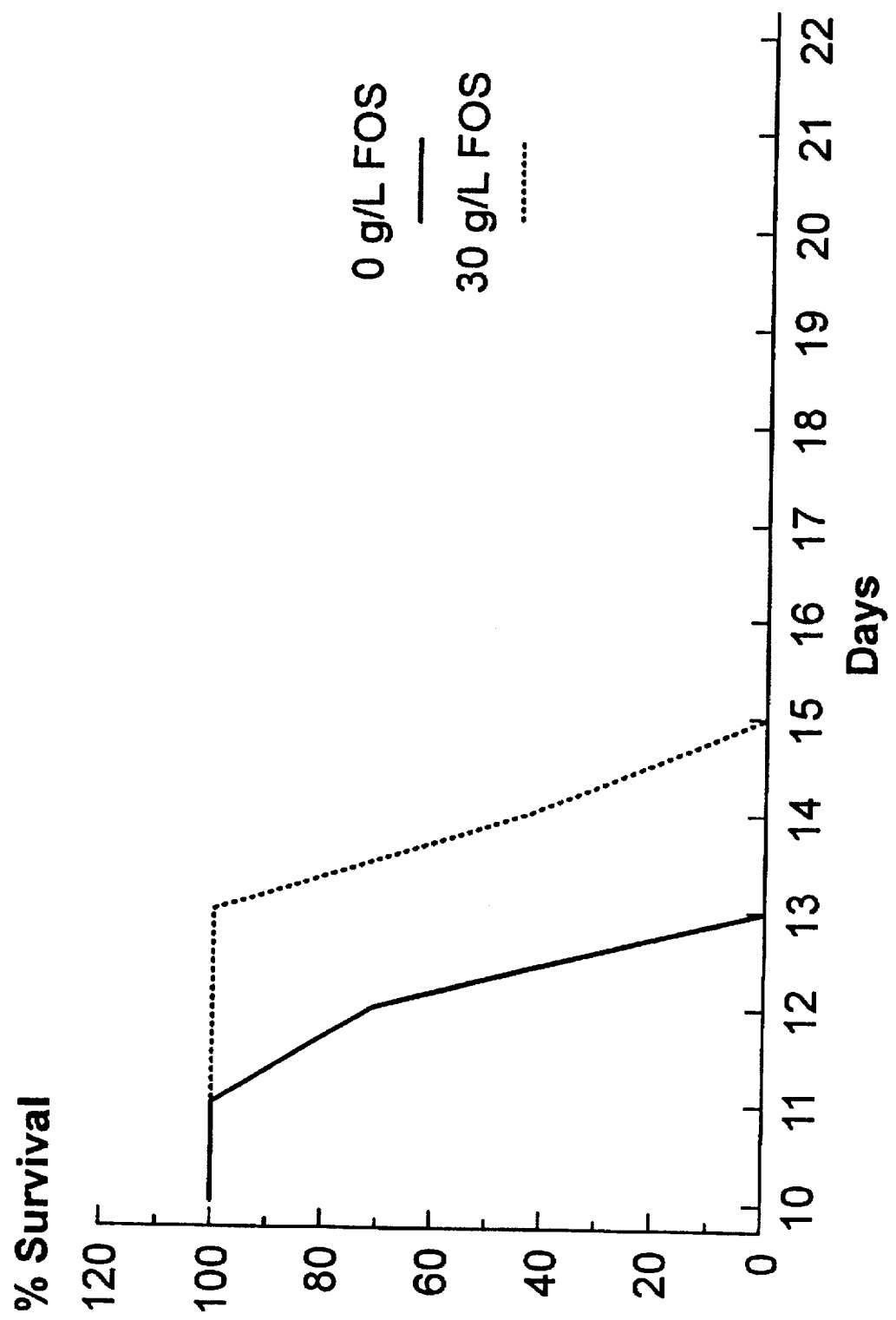

Median survival time (MST) for treatment groups are presented in Table 1. Overall, dietary supplementation with FOS (30 g/L in drinking water) tended to increase MST (P=0.09; log rank statistic) (Table 2). When using the Wilcoxon test, the overall effect of FOS was highly significant (P less than 0.01). If the comparison is made only in those hamsters which were not inoculated (allowing natural infection to occur) FOS did not improve MST (P greater than 0.20). As mentioned before, relying on natural infection can be inconsistent and thus inoculated animals were included in our experiments. When the comparison is made among those hamsters receiving C. difficile inoculation (0.5 and 2.0 mL), FOS had a highly significant effect (P less than 0.1) on MST. Furthermore, separating out the inoculation level (0.5 and 2.0 mL) resulted in a larger MST for hamsters receiving supplemental FOS (P less than 0.01). Survival curves for hamsters inoculated with 0.5 and 2.0 mL C. difficile are presented in FIGS. 3 and 4, respectively. These figures show the improved survival time of hamsters fed supplemental FOS. Overall, FOS tended to increase (P less than 0.10) median survival time (MST). In addition, MST was increased (P less than 0.01) for hamsters consuming FOS which were inoculated with 0.5 or 2.0 mL of C. difficile.

TABLE 1

MEDIAN SURVIVAL TIME (MST) OF
HAMSTERS FED (+/−) 30 g/L
FRUCTOOLIGOSACCHARIDES (FOS) IN DRINKING
WATER AND CHALLENGED WITH VARYING
LEVELS OF Clostridium difficile (2.0, 0.5, or 0 mL)

| GROUP # | n | INOCULATION PROTOCOL | FOS IN H$_2$O[1] | MST (DAYS) |
|---|---|---|---|---|
| 1 | 7 | 2.0 mL of ONC[2] | no | 13.0 |
| 2 | 7 | 0.5 mL of ONC | no | 14.0 |
| 3 | 7 | no inoculation | no | 15.0 |
| 4 | 7 | 2.0 mL of ONC | yes | 14.0 |
| 5 | 7 | 0.5 mL of ONC | yes | 16.0 |
| 6 | 6 | no inoculation | yes | 16.5 |

[1]FOS was provided at 30 g/L in the drinking water ad libitum. Approximate water consumption was 8 mL/hamster/day.
[2]ONC = Overnight culture of Clostridium difficile.

TABLE 2

MEDIAN SURVIVAL TIME (MST) OF
HAMSTERS FED (+/−) 30 g/L
FRUCTOOLIGOSACCHARIDES (FOS) IN DRINKING
WATER AND CHALLENGED WITH VARYING
LEVELS OF Clostridium difficile (2.0, 0.5, or 0 mL)

| Group | 30 g FOS/L | | Control (No FOS) | | Wilcoxon | log Rank |
|---|---|---|---|---|---|---|
|  | n | MST[1] | n | MST[1] | p-value | p-value |
| Overall | 20 | 15.0 | 21 | 14.0 | 0.007 | 0.09 |
| No inoculation | 6 | 16.5 | 7 | 15.0 | 0.51 | 0.97 |
| Inoculated[2] | 14 | 15.0 | 14 | 13.5 | <0.001 | <0.001 |
| 0.5 mL ONC[3] | 7 | 16.0 | 7 | 14.0 | 0.005 | 0.005 |
| 2.0 mL ONC | 7 | 14.0 | 7 | 13.0 | <0.001 | <0.001 |

[1]MST in days
[2]0.5 mL ONC + 2.0 mL ONC.
[3]ONC = Overnight culture of C. difficile.

EXPERIMENT 2

Figure 5:
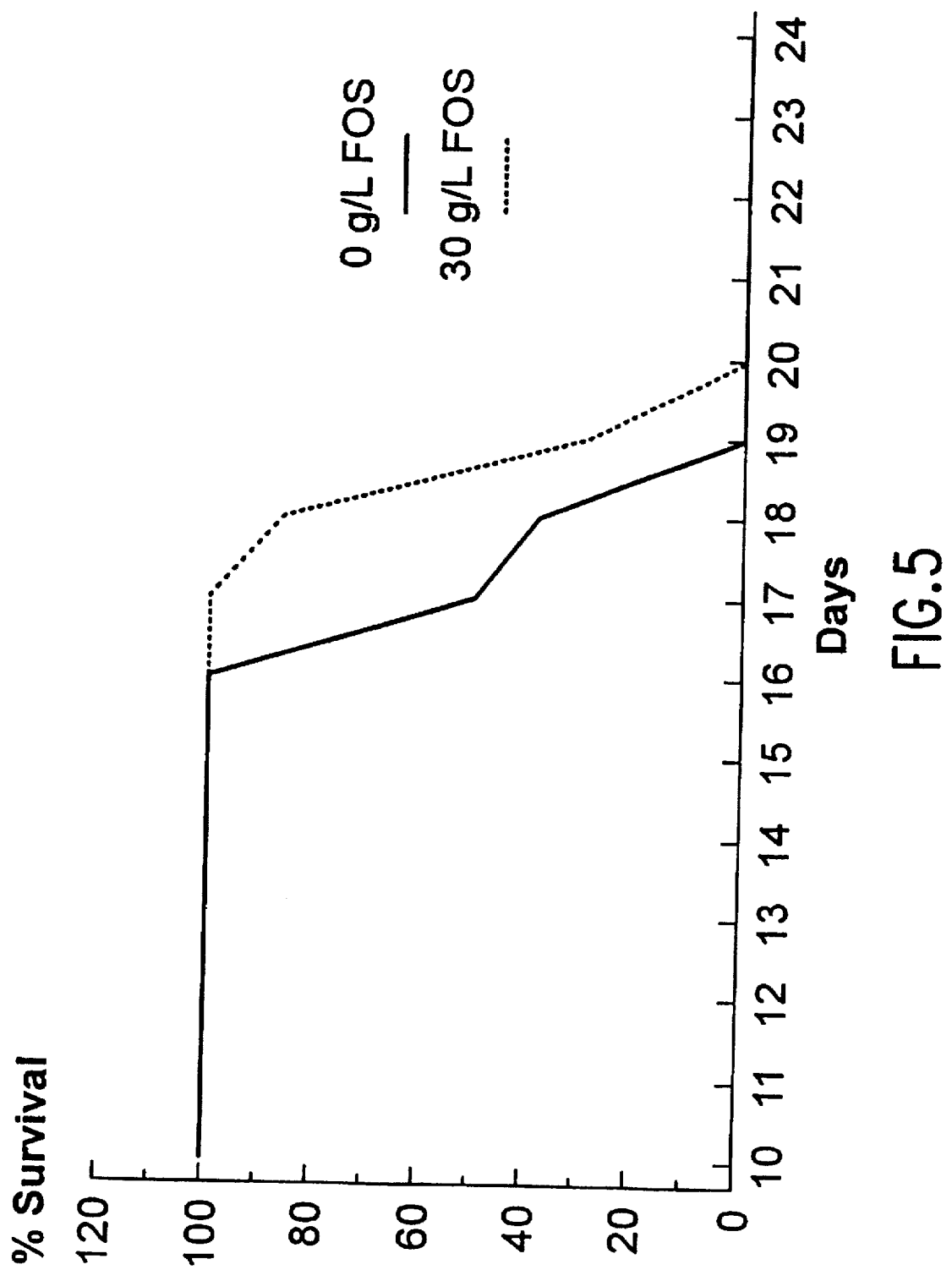
FIGS. 5 and 6 are graphic representations of the results of Experiment 2.
Figure 6:
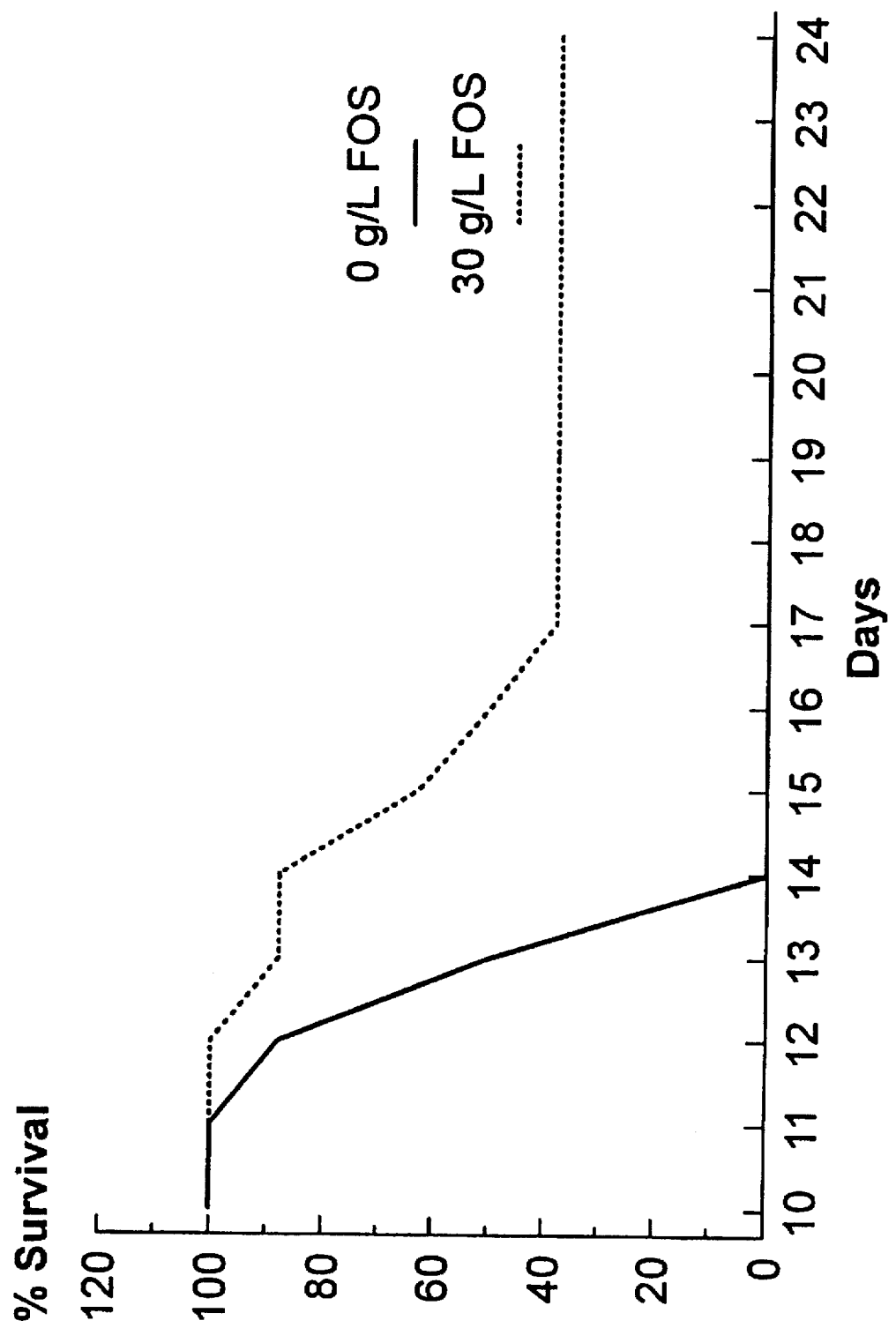
Figure 7:
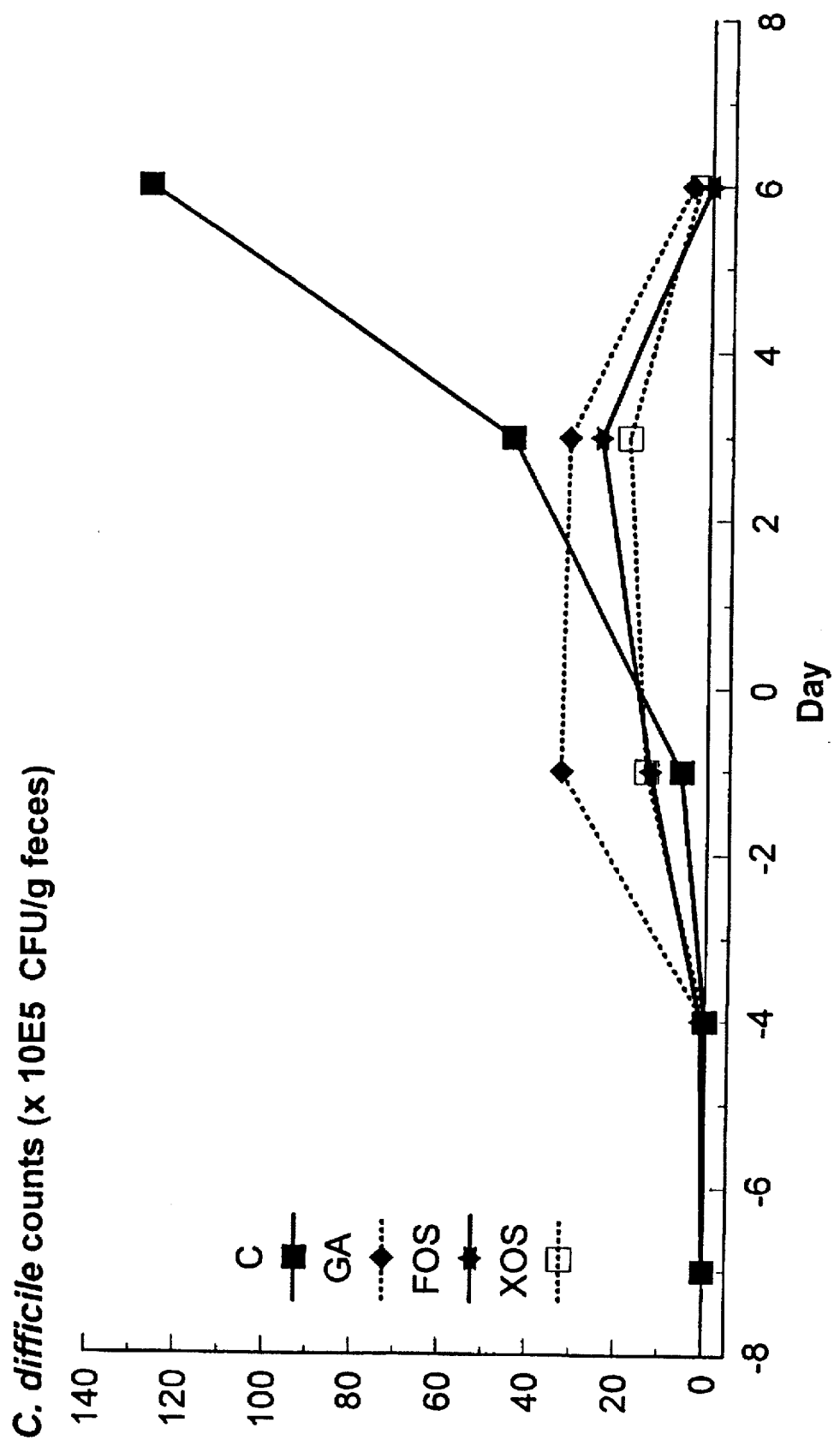
FIGS. 7 and 8 are graphic representations of the results of Experiment 3.
Figure 8:
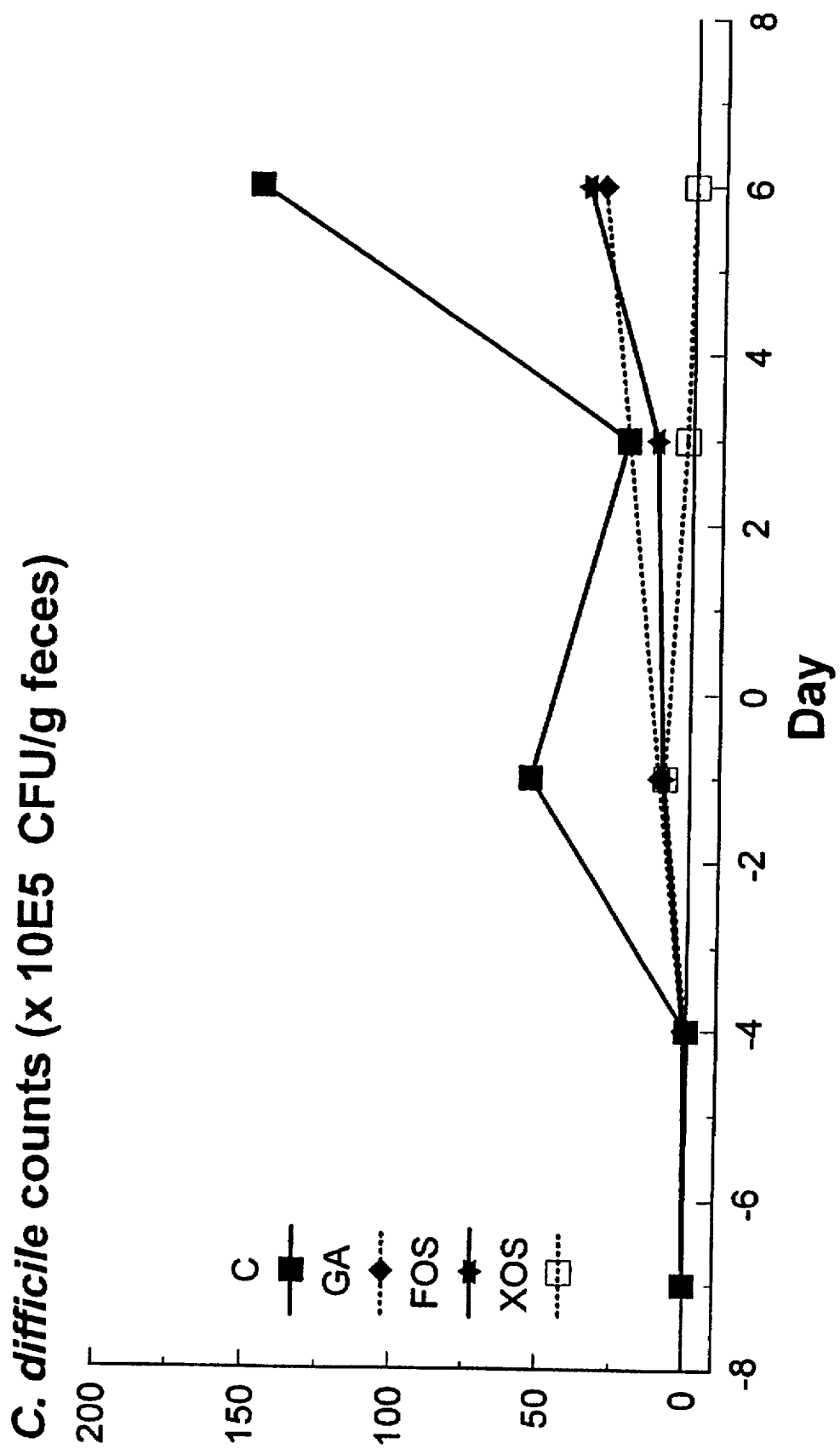

Median survival time for treatment groups are presented in Table 3. As in the previous experiment, the overall effect of FOS was to increase MST of hamsters (P less than 0.05). In this experiment, there appeared to be an interaction between the Vancomycin treatment and inoculation level (Table 4). Hamsters supplemented with FOS and inoculated with C. difficile but not treated with Vancomycin tended to have improved MST (P less than 0.10). However, FOS had no effect (P greater than 0.20) on inoculated hamsters treated with Vancomycin. On the other hand, FOS supplementation increased MST of non-inoculated hamsters treated or not treated with Vancomycin (P less than 0.05 and P less than 0.01, respectively; survival curves, FIG. 5 and 6, respectively). Again, survival curves show the added benefits of FOS. Overall, hamsters fed FOS had increased (P less than 0.05) MST. These data suggest that dietary supplementation with FOS increases median survival time in a hamster model of Clostridium difficile-colitis.

TABLE 3

MEDIAN SURVIVAL TIME (MST) OF
HAMSTERS FED (+/−) 30 g/L
FRUCTOOLIGOSACCHARIDES (FOS) IN DRINKING
WATER AND CHALLENGED WITH VARYING
LEVELS OF Clostridium difficile, AND
TREATED (+/−) WITH VANCOMYCIN

| Group # | n | Inoculation[1] | FOS in H$_2$O[2] | Vancomycin | MST (days) |
|---|---|---|---|---|---|
| 1 | 8 | yes | no | no | 13.0 |
| 2 | 8 | yes | no | yes | 20.0 |
| 3 | 8 | no | no | yes | 17.5 |
| 4 | 8 | no | no | no | 13.5 |
| 5 | 8 | yes | yes | no | 14.5 |
| 6 | 8 | yes | yes | yes | 19.0 |
| 7 | 7 | no | yes | yes | 19.0 |
| 8 | 8 | no | yes | no | 16.5 |

[1]Inoculated with an overnight culture of Clostridium difficile (2.0 mL).
[2]FOS was provided at 30 g/L in the drinking water, ad libitum. Approximate water consumption was 8 mL/hamster/day.

TABLE 4

MEDIAN SURVIVAL TIME (MST) OF
HAMSTERS FED (+/−) 30 g/L
FRUCTOOLIGOSACCHARIDES (FOS) IN DRINKING
WATER, CHALLENGED (+/−) WITH
Clostridium difficile, AND
TREATED (+/−) WITH VANCOMYCIN

| Group[1] | 30 g/L FOS | | CONTROL | | Wilcoxon | log Rank |
|---|---|---|---|---|---|---|
|  | n | MST[2] | n | MST[2] | p-value | p-value |
| Overall | 31 | 18.0 | 32 | 16.0 | 0.027 | 0.020 |
| N, No Vanco | 8 | 16.5 | 8 | 13.5 | 0.003 | 0.001 |
| N, Vanco | 7 | 19.0 | 8 | 17.5 | 0.021 | 0.026 |
| I, No Vanco | 8 | 14.5 | 8 | 13.0 | 0.07 | 0.054 |
| I, Vanco | 8 | 19.0 | 8 | 20.0 | 0.66 | 0.95 |
| N | 15 | 19.0 | 16 | 15.5 | 0.007 | 0.005 |
| I | 16 | 16.5 | 16 | 16.5 | 0.43 | 0.41 |
| No Vanco | 16 | 15.5 | 16 | 13.5 | 0.001 | <0.001 |
| Vanco | 15 | 19.0 | 16 | 19.0 | 0.49 | 0.37 |

[1]I = Inoculation with an overnight culture of C. difficile, N = no inoculation, Vanco = Vancomycin.
[2]MST in days In general, the results of Experiments 1 and 2 show that enteral administration of a therapeutically effective mount of an indigestible oligosaccharide (FOS) inhibits the infection of a mammal by C. difficile as shown by improved survival times in a hamster model of C difficile-colitis. This has been shown by an increase in survivability (in certain treatment groups) and a consistent increase in median survival time. Impressively, the improved survival time due to FOS supplementation was above the effect of fiber contained in the chow diet.

EXPERIMENT 3

The objective of Experiment 3 was to determine the effect of feeding highly fermentable carbohydrate on *C. difficile* infection in a murine model that included antibiotic administration prior to pathogen (*C. difficile*) challenge. The model involved the disruption of gut microbiota with the antibiotic cefoxitin followed by a challenge with *C. difficile* (VPI 10463).

MATERIALS AND METHOD

Animals

Sixty-four male BALB/c mice (mean body weight 19.3±1.6 g) were individually housed in stainless steel cages. Environmental conditions were controlled to provide a 12 h light cycle and a constant temperature of 24° C.

Diets

Water and a nutritionally balanced, low residue, diet powder (Ensure™) were provided ad libitum. Control mice (C) received no fiber supplement. Three fermentable carbohydrate sources were provided to the remaining groups. The gum arabic (GA; a powder) and fructooligosaccharides (FOS; a powder) were mixed with the Ensure™ diet (44 mg fiber/g diet powder). Xylooligosaccharides (XOS; a syrup) were mixed with drinking water (30 g/L).

Bacterial strains and conditions

A known toxigenic strain of *Clostridium difficile* was used in this study. Wilson et al., "Gnotobiotic models for study of microbial ecology of *Clostridium difficile* and *Escherichia coli*", THE JOURNAL OF INFECTIOUS DISEASES, 153 (3):547–551 (1986); Sullivan et al., "Purification and characterization of toxins A and B of *Clostridium difficile*", INFECTION AND IMMUNITY, 35 (3): 1032–1040 ( 1982). The organism was maintained and grown in reinforced clostidial medium (RCM; Difco, Detroit, Mich., U.S.A.) and standard cell suspensions used as inocula. All diluents and media were prepared using routine anaerobic techniques. Mackie et al., "Enumeration of anaerobic bacterial microflora of the equine gastrointestinal tract", APPLIED AND ENVIRONMENTAL MICROBIOLOGY, 54(9):2155–2160 and "insacculus" to be -in sacculus (1988); Meyer et al., "Microbiological evaluation of the intraruminal insacculus digestion technique", APPLIED ENVIRONMENTAL MICROBIOLOGY, 51(3):622–629, (1986).

EXPERIMENTAL DESIGN

All 64 mice consumed Ensure™ powder for three days. On day four all mice received 100 μg cefoxitin/g body weight orogastrically. Cefoxitin (Sigma Chemical Co., St. Louis, Mo., U.S.A.) was dissolved in water and the proper dose was delivered into the stomach with a gavage needle (22 ga, 1 in). The following day, mice were randomly assigned to either the control or different fermentable carbohydrate treatments and were fed their respective diets for five days. At this time, eight mice per diet were inoculated as described above with 200 μl of a *C. difficile* suspension containing $2.8 \times 10^8$ colony forming units (CFU)/mL. The RCM was used to inoculate the remaining 8 mice on each diet. Sacrifice by $CO_2$ asphyxiation occurred six days following inoculation. The entire animal protocol was completed in 15 days.

DATA COLLECTION AND STATISTICS

Five fecal samples were collected throughout the experiment (days 2, 5, 8, 12, and 15). For clarity, these sampling days are expressed relative to *C. difficile* inoculation (day 0) and are thus days -7, -4, -1, 3 and 6. One hundred mg feces was collected from each animal and immediately suspended in 9.9 mL anaerobic diluent. Bryant et al., "cultural methods and some characteristics of some of the more numerous groups of bacteria in the bovine rumen", JOURNAL OF DAIRY SCIENCE, 36:205–217 (1953). Fecal samples were evaluated using the following response criteria: numbers of *C. difficile* of cycloserine-cefoxitin-fructose selective agar. George et al., "Selective and differential medium for isolation of *Clostridium difficile*", JOURNAL OF CLINICAL MICROBIOLOGY, 9:214–219 (1979); toxin A titer using an enzyme-linked immunosorbent assay (Tox-A-Test, TECHLAB; Blacksburg, Va., U.S.A.).

The treatments were arranged as a randomized complete block within a split-plot design. Gill et al., "Analysis of repeated measurements of animals", JOURNAL OF ANIMAL SCIENCES, 33:331–336 (1971). Data were subjected to analysis of variance according to the General Linear Models (GLM) procedure of SAS. SAS Institute, "SAS User's Guide: Statistics", SAS Institute, Inc., Cary, N.C., (1988). Treatment effects were tested using an F-statistic and a P value of 0.05 was chosen as the significance level.

RESULTS AND DISCUSSIONS

Fecal counts of *C. difficile* (Table 5) were influenced by a diet x sampling day interaction (P<0.01). At the onset of the experiment (day -7) there were no detectable counts of *C. difficile* ($<10^4$ CFU/g feces). Interestingly, after cefoxitin dosage (day -6) and by three days following pathogen inoculation, all mice, including the uninoculated mice, became infected with *C. difficile* to a certain degree. For mice fed the control diet, *C. difficile* continued to increase throughout the experiment. By six days post *C. difficile* inoculation, the control mice had the highest *C. difficile* counts ($127.5 \times 10^5$ CFU/g feces) and mice fed FOS had the lowest counts (0).

During the experimental period, toxin A assays were performed on fecal samples and incidence (percentage of mice with detectable toxin A) and toxin A titer are presented (Table 6). Before *C. difficile* inoculation, no toxin A was detected in feces from any mice. By three days following Inoculation, *C. difficile* and toxin A were detected in virtually every mouse and those inoculated with *C. difficile* had the highest tilers ($10^4$). Six days post inoculation, mice consuming the C and GA diets had greater than a 50% incidence of toxin A while mice consuming FOS and XOS had less than a 50% incidence of toxin A. Only mice consuming C or GA diets and inoculated with *C. difficile* developed severe diarrhea (37 and 75%, respectively) or died (12.5 and 50%, respectively).

TABLE 5

EFFECT OF DIET, SAMPLING DAY, AND INOCULATION ON *Clostridium difficile* IN FECES

| Treatments[3] | Sampling Day[2] | | | | |
|---|---|---|---|---|---|
| | -7 | -4 | -1 | 3 | 6 |
| C+ | $<10^4$ | 0.1[b] | 5.8[c] | 44.4[a] | 127.5[a] |
| C- | $<10^4$ | 0.1[b] | 53.9[a] | 22.0[ab] | 147.6[a] |
| GA+ | $<10^4$ | 0.1[b] | 32.9[b] | 31.6[b] | 4.3[c] |
| GA- | $<10^4$ | 1.2[a] | 10.3[c] | 21.6[ab] | 30.9[b] |
| FOS+ | $<10^4$ | 1.1[a] | 12.8[c] | 24.5[ab] | 0.0[c] |
| FOS- | $<10^4$ | 0.9[a] | 8.8[c] | 11.9[b] | 36.3[b] |
| XOS+ | $<10^4$ | 0.0[b] | 13.7[c] | 18.1[b] | 2.5[c] |
| XOS- | $<10^4$ | 0.1[b] | 8.3[c] | 1.9[c] | 0.0[c] |

[1]*C. difficile* counts ($\times 10^5$ CFU/g feces) determined on cycloserine-cefoxitin-egg yolk agar. Data exhibited a diet x sampling day interaction; means in a column with unlike superscripts are different (P < .01).
[2]Fecal sampling days relative to pathogen inoculation (day 0).

TABLE 5-continued

**EFFECT OF DIET, SAMPLING DAY, AND INOCULATION ON *Clostridium difficile* IN FECES**

| Treatments[3] | Sampling Day[2] | | | | |
|---|---|---|---|---|---|
| | −7 | −4 | −1 | 3 | 6 |

[3]Control (C); gum arabic (GA); fructooligosaccharides (FOS); xylooligosaccharides (XOS) with (+) or without (−) 200 μl inoculation of *Clostridium difficile* VPI 10463 (2 × 10[8] CFUs/mL).

TABLE 6

**INCIDENCE AND TOXIN TITER FOR *Clostridium difficile* TOXIN A[1]**

| Treatments[3] | Sampling Day[2] | | |
|---|---|---|---|
| | −1 | 3 | 6 |
| C+ | 0 | 62.5 | 75.0 |
| C− | 0 | 62.5 | 87.5 |
| GA+ | 0 | 12.5 | 50.0 |
| GA− | 0 | 87.5 | 100.0 |
| FOS+ | 0 | 62.5 | 37.5 |
| FOS− | 0 | 50.0 | 50.0 |
| XOS+ | 0 | 87.5 | 37.5 |
| XOS− | 0 | 25.0 | 37.5 |
| Titer[4]+ | nd | 10[4] | 10[4] |
| Titer− | nd | 10[3] | 10[3] |

[1]Percentage of mice having detectable titers of toxin A in feces.
[2]Fecal sampling days relative to pathogen inoculation (day 0).
[3]Control (C); gum arabic (GA); fructooligosaccharides (FOS); xylooligosaccharides (XOS) with (+) or without (−) 200 μl inoculation of *Clostridium difficile* VPI 10463 (2 × 10[8] CFUs/mL).
[4]Titer of toxin A expressed as the reciprocal of the highest dilution in which toxin A was detected in fecal samples, nd = not detected. Titers are pooled across diets.

CONCLUSION

EXPERIMENT 3

While mice do not develop the same lesions as do humans (PMC) a murine model can still provide meaningful in vivo data. Studies of microbial interactions coupled with nutritional manipulations can contribute to the understanding of causative factors in *C. difficile* colonization and infection. Moreover, the information provides a better understanding of gastrointestinal microbial ecology. In this study, the ologosaccharides suppressed growth of *C. difficile* and appeared to provide protection to the intestinal epithelial tissue.

The present invention provides a method of inhibiting the infection of a mammal by *C. difficile* by enterally administering a therapeutically effective amount of an indigestible oligoccharide, and/or inhibiting the level of toxin A from *C. difficile*. As used herein "inhibiting" is understood to refer to both reducing the number of *C. difficile* and preventing an increase in the number of *C. difficile*. The indigestible oligosaccharide may be one or more fructooligosaccharides, (such as 1-ketose, nystose, or $1^F$-β-fructofuranosyl nystose), and/or one or more xylooligosaccharides, (such as xylobiose, xylotriose, or xylotetrose).

We claim:

1. A method of inhibiting the infection of a mammal by *Clostridium difficile* by enterally administering a therapeutically effective amount of an indigestible oligosaccharide selected from the group consisting of fructooligosaccharides.

2. The method of claim 1 wherein said fructooligosaccharide is selected from the group consisting of 1-ketose, nystose and $1^F$-β-fructofuranosyl nystose fructooligosaccharides.

3. A method of inhibiting the level of toxin A from *Clostridium difficile* in a mammal by enterally administering a therapeutically effective amount of an indigestible oligosaccharide selected from the group consisting of fructooligosaccharides.

4. The method of claim 3 wherein said fructooligosaccharide is selected from the group consisting of: 1-kestose, nystose and $1^F$-β-fructofuranosyl nystose fructooligosaccharides.

5. A method of inhibiting the infection of a mammal by *Clostridium difficile* by enterally administering a therapeutically effective amount of a fructooligosaccharide selected from the group consisting of 1-kestose, nystose and $1^F$-β-fructofuranosyl nystos fructooligosaccharides.

* * * * *